United States Patent [19]

West

[11] Patent Number: 5,549,264

[45] Date of Patent: Aug. 27, 1996

[54] SUPPORT POLE LIFT MECHANISM

[75] Inventor: Richard L. West, Lake Villa, Ill.

[73] Assignee: Baxter International Inc., Deerfield, Ill.

[21] Appl. No.: 270,645

[22] Filed: Jul. 1, 1994

[51] Int. Cl.$^6$ .................................................. F16M 11/00
[52] U.S. Cl. .......................... 248/157; 248/161; 312/209; 312/319.1
[58] Field of Search ........................ 248/157, 132, 248/161, 162.1, 123.1, 414, 919, 917, 918; 267/165, 156; 210/232, 141, 360.1; 312/209, 249.8, 319.1

[56] References Cited

U.S. PATENT DOCUMENTS

| | | | |
|---|---|---|---|
| 2,961,260 | 11/1960 | Newlin | 248/161 |
| 3,014,682 | 12/1961 | Veneman | 248/161 |
| 3,890,907 | 6/1975 | Peterson | 248/571 X |
| 4,817,903 | 4/1989 | Braechler et al. | 248/919 X |
| 5,016,846 | 5/1991 | Solomon | 248/161 |
| 5,056,278 | 10/1991 | Atsukawa | 248/161 X |
| 5,090,648 | 2/1992 | Wood, IV | 248/354.5 X |
| 5,324,011 | 6/1994 | Vilches et al. | 267/156 |
| 5,348,324 | 9/1994 | Trotta | 108/144 X |

Primary Examiner—Ramon O. Ramirez
Attorney, Agent, or Firm—Daniel D. Ryan; Bradford R. L. Price; Joseph B. Barrett

[57] ABSTRACT

A support assembly for process control equipment includes a cabinet containing processing equipment. A vertical support pole is supported on said cabinet through a collar for extension and retraction. Process control equipment such as electronic control equipment and a video monitor is mounted on the upper end of the pole. At least one, and preferably two, constant force springs biased into a fully coiled position are attached at one end to the lower end of the pole. The opposite end of the springs are mounted for free rotation on a spool which is secured to the cabinet, whereby raising and lowering of the process control equipment is facilitated.

4 Claims, 5 Drawing Sheets

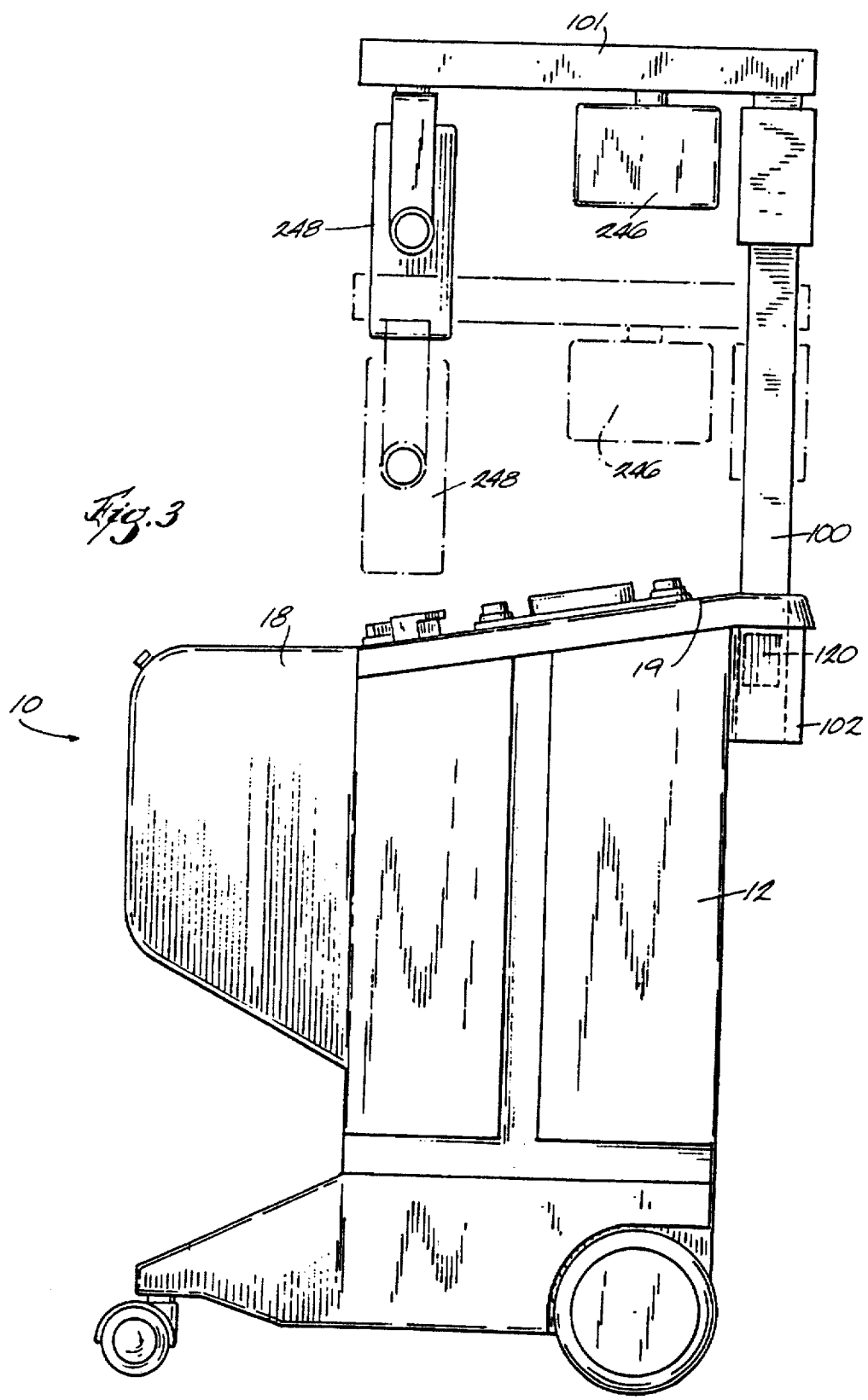

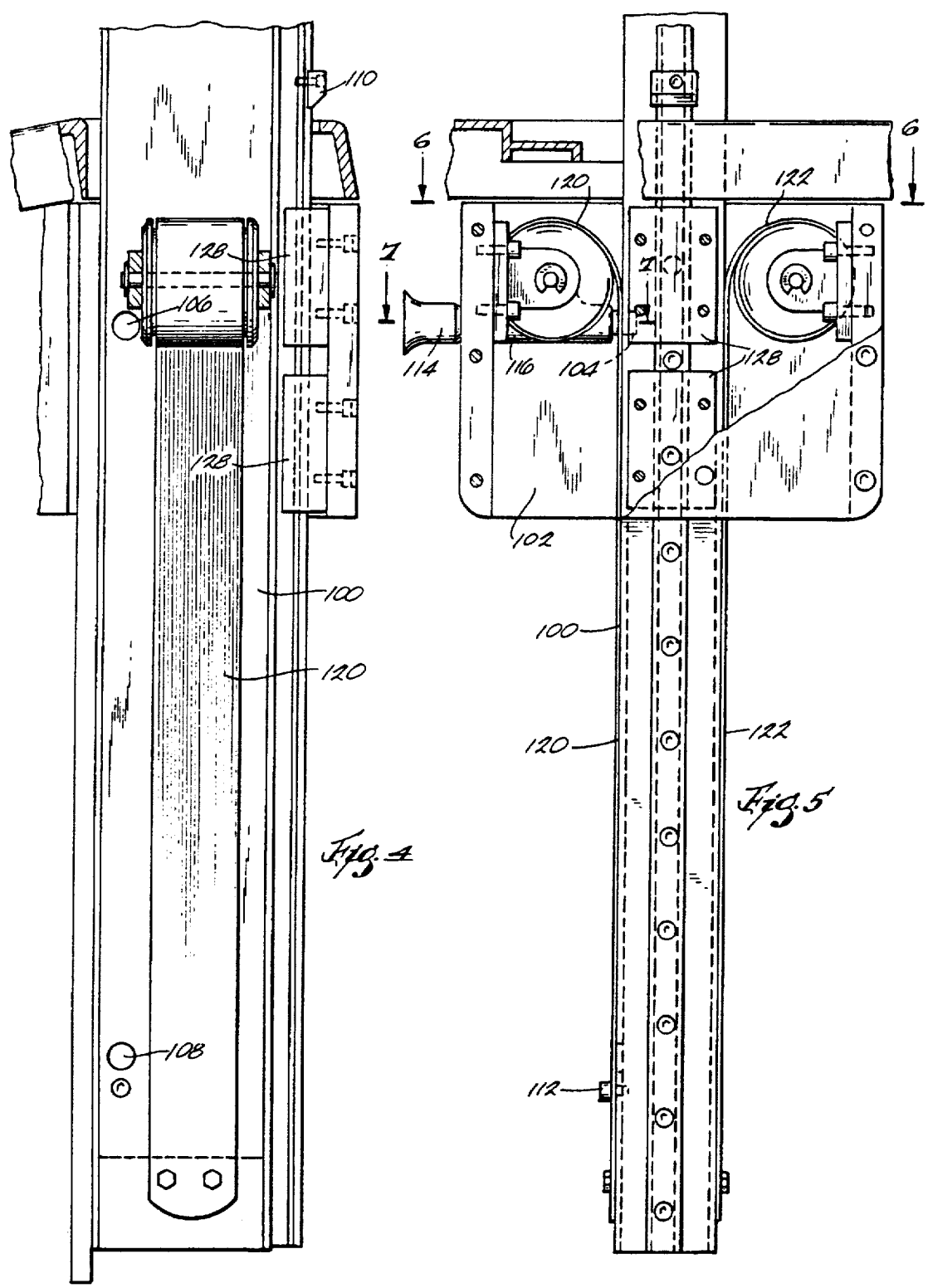

5,549,264

SUPPORT POLE LIFT MECHANISM

FIELD OF THE INVENTION

The present invention relates to a lift mechanism for process controllers. More specifically, the invention relates to an improved lift assisting device for support poles on centrifuges for supporting process controllers and video terminals of the type used as input/output terminals on such process controllers.

BACKGROUND OF THE INVENTION

Blood processing equipment such as centrifuges which are conventionally used to separate the blood into its various constituents such as red blood cells, platelets and plasma require sophisticated and complex process control equipment. Such process controllers often take the form of an electronic controller provided with an input/output CRT terminal. It is desirable that such equipment be extendable to a lifted position during use, and it is capable of being lowered to a storage position during transport or storage of the equipment.

A simple and economical device is needed to assist in lifting of the process control mechanism so that it can be handled by hospital personnel who may not have sufficient or physical or lifting strength to lift heavy objects, particularly to an elevated position which may be somewhat above the head of the operator. When conventional springs are used to provide such lifting assistance, the problem exists of the spring being under increasingly greater tension as the mechanism is lowered. Thus, excessive upward force is applied on the mechanism when it is first released. This raises the possibility of injury to personnel or damage to the equipment being supported.

A need has, thus, existed for a lift mechanism for supporting poles which is both economical and effective in lifting of the equipment.

It is an object of the present invention to provide a lift assisting mechanism for supporting poles used on blood processing equipment. In accordance with an important aspect of the invention, such a lift mechanism is provided which is economical but which provides a uniform lifting force to the mechanism as it is raised and lowered.

In accordance with a further aspect of the invention, a pole lift mechanism is provided which utilizes at least one constant force spring and preferably two of such springs to provide an even and uniform lift assisting force on the mechanism. In accordance with a yet further aspect of the invention, the supporting pole is provided with such constant spring lift mechanisms which work in conjunction with a series of bearings which facilitate raising and lowering of the supporting pole.

Briefly, a support assembly for process control equipment according to the invention includes a cabinet containing processing equipment. A vertical support pole is supported on said cabinet through a collar for extension and retraction. Process control equipment such as electronic control equipment and a video monitor is mounted on the upper end of the pole. At least one, and preferably two constant force springs biased into a fully coiled position are attached at one end to the lower end of the pole. The opposite end of the springs are mounted for free rotation on a spool which is secured to the cabinet, whereby raising and lowering of the process control equipment is facilitated.

Further objects and advantages of the invention will become apparent from the following detailed description, the claims and the accompanying drawings.

BRIEF DESCRIPTION OF THE DRAWINGS

FIG. 3 is a side elevational view of the mechanism of FIG. 1 showing the process controller by phantom lines in the lowered position;

FIG. 4 is a fragmentary view of a supporting pole and lift assist spring mechanism viewed from the side in the fully extended position;

FIG. 5 is a rear fragmentary rear elevational view of the mechanism shown in FIG. 4;

DETAILED DESCRIPTION OF A PREFERRED EMBODIMENT

Figure 1:
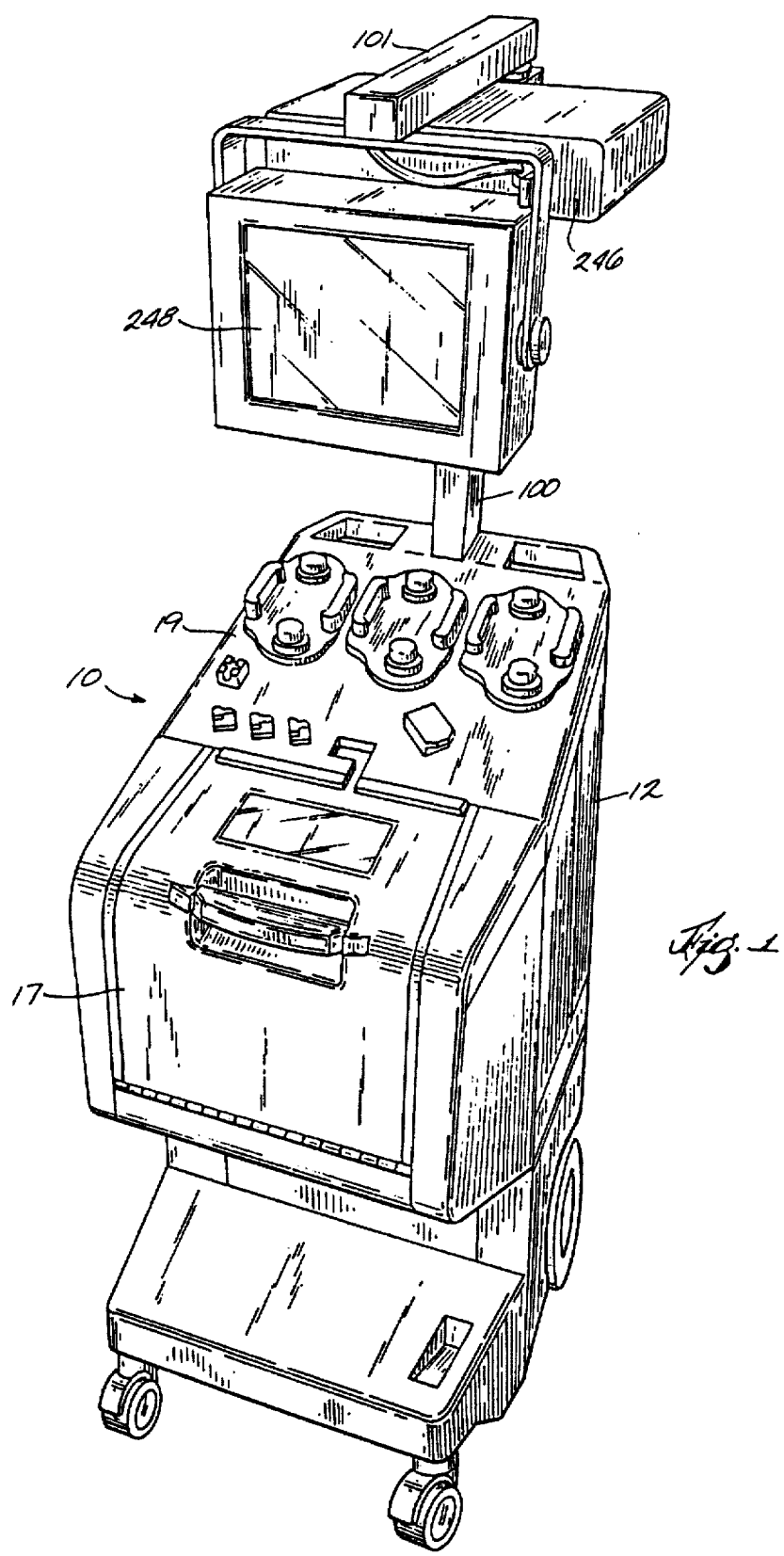
FIG. 1 is a perspective view of a blood centrifuge device embodying the invention.
Figure 2:
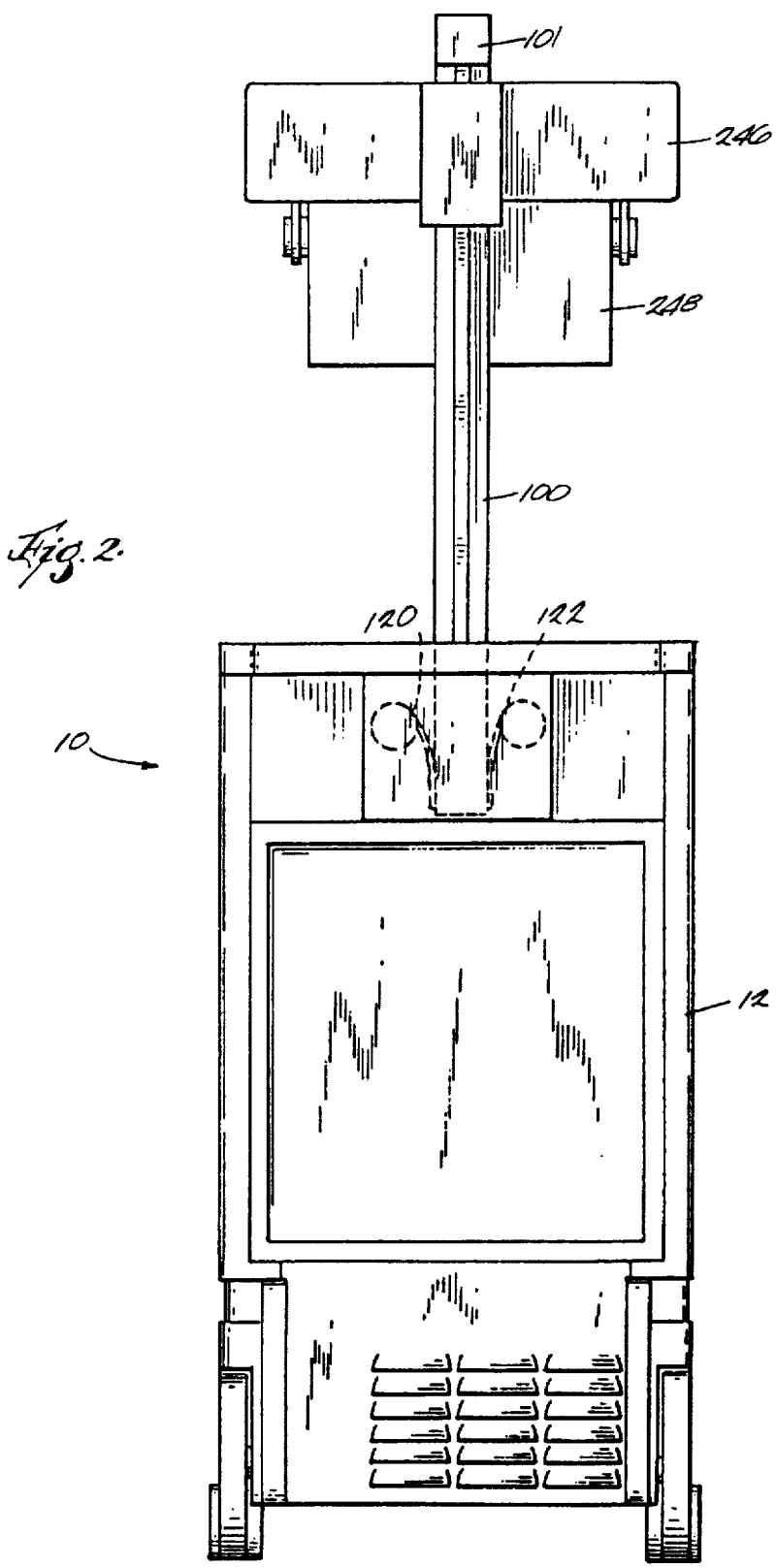
FIG. 2 is a rear elevational view of the device shown in FIG. 1.

Referring more specifically to the drawings, FIGS. 1 through 3 show a centrifugal processing system 10 that embodies the features of the invention. The system 10 can be used for processing various fluids. The system 10 is particularly well suited for processing whole blood and other suspensions of biological cellular materials. Accordingly, the illustrated embodiment shows the system 10 used for this purpose.

The system 10 includes a centrifuge assembly 12 (see FIG. 1) and a fluid processing assembly (not shown) used in association with the centrifuge assembly.

The centrifuge assembly 12 is intended to be a durable equipment item capable of long term, maintenance free use. The fluid processing assembly is a single use, disposable set loaded on the centrifuge assembly 12 at time of use in accordance with known practices. The operator removes the fluid processing assembly from the centrifuge assembly 12 upon the completing the procedure and discards it.

A centrifuge or processing chamber is provided within the assembly 12 and is accessible through a cover 18. In use, the centrifuge assembly 12 rotates the processing chamber to centrifugally separate blood components. The construction of the processing chamber can vary, with numerous constructions being known in the art.

The processing assembly 12 includes an array of flexible tubing that forms a fluid circuit which conveys liquids to and from the processing chamber. The fluid circuit includes one or more in line fluid processing containers and devices, as is known in the art, in association with pump and valve stations on the centrifuge assembly 12 to direct liquid flow among the multiple liquid sources and destinations during a blood processing procedure. The assembly 12 thereby forms an integral, sterile unit.

The processing chamber can be variously constructed. For example, it can be constructed like the double bag processing chambers shown in Cullis et al., U.S. Pat. No. 4,146,172. Specific details of the construction of the processing chamber 14 and other components of the system are not essential to an understanding of the invention and can be also be found in U.S. patent application Ser. No. 07/965,074, filed Oct. 22, 1992, abandoned and entitled "Enhanced Yield Blood Processing Systems and Methods Establishing Vortex Flow Conditions", which is incorporated herein by reference.

The centrifuge assembly 12 includes a processing controller 246. The controller 246 governs the operation of the centrifuge assembly 12. The processing controller 246 preferably includes an integrated input/output terminal 248 as seen in FIG. 1), which receives and display information relating to the processing procedure. Controller 246 and terminal 248 are supported on vertical support pole 100 by means of a mounting bracket 101.

It is preferred to place the stationary functional components such as pumps, sensors, detectors, and the like for convenient access on the panel 19 by the user. Most preferably, these items are positioned at about the elevation of the waist of the average person.

Statistics providing quantitative information about the location of this preferred access zone for a range of people (e.g., Large Man, Average Man/Large Woman, Average Adult, Small Man/Average Woman, etc.) are found in the Humanscale™ Series Manuals (Authors: Niels Diffrient et al., a Project of Henry Dreyfuss Associates), published by the MIT Press, Massachusetts Institute of Technology, Cambridge, Mass.

Further details of the chamber assembly are found in U.S. patent application Ser. No. 07/814,403, filed Dec. 23, 1991, abandoned and entitled "Centrifuge with Separable Bowl and Spool Elements Providing Access to the Separation Chamber", which is incorporated herein by reference.

Processing controller 246 and input/output terminal 248 are supported on a vertical support pole 100. Support pole 100 is movably supported within a collar 102 so that it can be moved between an elevated position shown in FIGS. 1–3 and lowered to the lowered position shown by phantom lines in FIG. 3. Due to the weight of the components being supported, it is difficult for the average person to safely raise the support pole without assistance.

A spring biased retractable locking pin 104 is provided to releasably position pole 100 in either the upper or lower position. For this purpose, receiving openings 106 and 108 are provided on the pole to lockingly receive the end of pin 104. Pin 104 which is mounted in an opening 103 in collar 102. It will be apparent that additional receiving holes similar to 106 and 108 can be provided if more than two vertical positions are desired for the components being supported on pole 100. In the preferred embodiment it is also preferred that projections 110 and 112 be provided to act as maximum down and up stops, respectively, to limit the upward and downward motion of pole 100.

Figure 7:
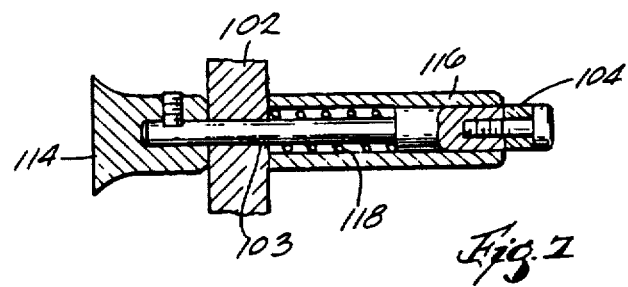
FIG. 7 is a sectional view of a releasable stop mechanism used in connection with the invention.

As best seen in FIG. 7, pin 104 is provided with a knob 114 and is retractably positioned within a supporting cylinder 116. The pin 104 is biased into the extended position by a coil spring 118 as seen in FIG. 7.

Attached to each side of support pole 100 at its lower end is one end of a constant force spring 120 and 122, respectively. Springs 120 and 122 are mounted for free rotation upon spools 124 and 126, respectively. Each of the springs 120 and 122 is in the form of a stiff coil of spring material that is biased to return to the fully coiled position. Considerable force is required to straighten the springs. The stiffness and weight of the springs is dictated by the weight of the components supported at the top of support pole 100. Due to the fact that springs 120 and 122 are biased to return to the upward position, they serve to provide a constant upward force on pole 100 as it is raised or lowered, thus, facilitation easy movement thereof.

Figure 6:
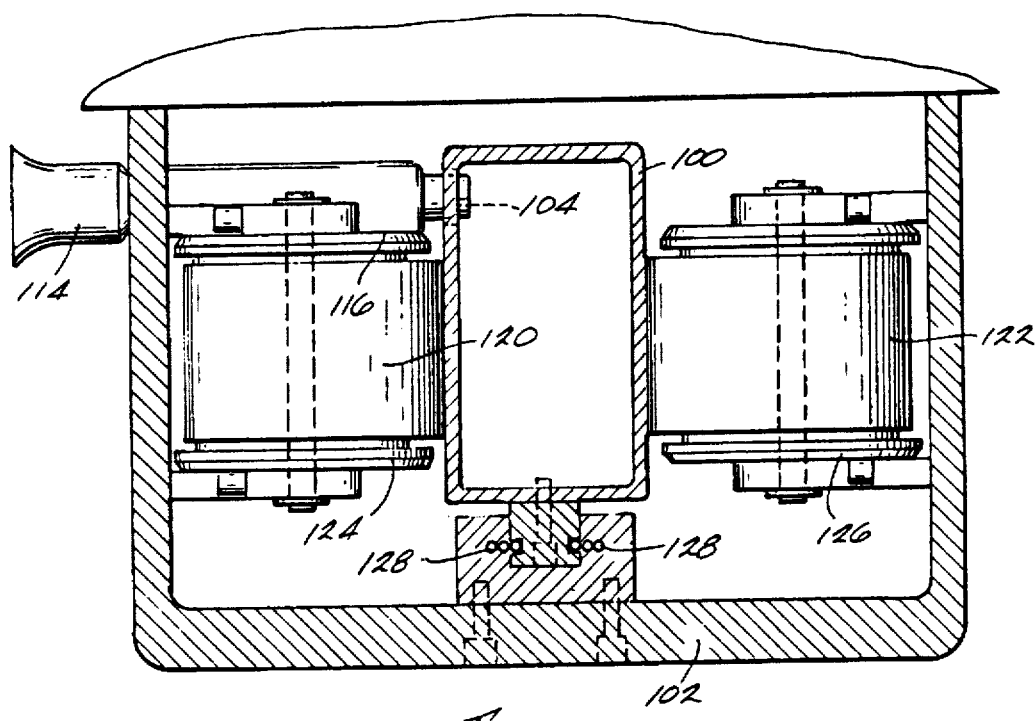
FIG. 6 is a sectional view taken along line 6—6 of FIG. 5.

As seen in FIG. 6, pole 100 is mounted for ease of movement on collar 102 by means of bearings 128 which facilitate movement of pole 100 upwardly and downwardly. While it is preferred to use two constant force springs, it will be really apparent to those skilled in the art that the benefits of the invention could be achieved by the use of a single such spring or a greater number than two, three or four such springs.

Although the present invention has been described in considerable detail with reference to certain preferred versions thereof, other versions are possible, therefore the scope of the appended claims should not be limited to the description of the preferred embodiments described above.

What is claimed is:

1. A support pole assembly comprising:

a base including a support collar, a vertical support pole having an upper weight bearing end and a lower end, the support pole being carried within the collar for movement within the collar between a fully raised position in which the upper weight bearing end is located at a first position above the base and a fully lowered position in which the upper weight bearing end is located at a second position above the base closer to the base than the first position, and a lifting mechanism for the support pole comprising
a spool mounted on the collar for rotation about an axis,
a first spring element having a first end attached to the support pole adjacent the lower end and a second end attached to the spool, the first spring element being biased into a coiled condition about the spool when the support pole is in its fully raised position, the first spring element being progressively placed in an uncoiled condition about the spool as the support pole is progressively moved toward the fully lowered position to apply a normal bias to the support pole toward the fully raised position, an interior guide passage in the collar including an interior end aligned with the support pole, the support pole including a first positioning aperture aligning with the interior end of the guide passage when the support pole is in a desired raised position below the fully raised position and a second positioning aperture aligning with the interior end of the guide passage when the support pole is in a desired lowered position above the fully lowered position, a pin carried by the guide passage, the pin including an operative end movable inside the collar within the guide passage between an extended position outside the interior end of the guide passage and a retracted position inside the guide passage, a second spring element within the guide passage coupled to the pin to apply a normal bias to the operative end of the pin toward the extended position and into engagement with the first and second positioning apertures when the support pole moves, respectively, into the desired raised and lowered positions, the normal bias of the second spring element overcoming the normal bias of the first spring element to releasably hold the support pole in the desired raised and lowered positions, and the pin including a handle end exposed for manipulation outside the collar to move the operative end of the pin against the normal bias of the second spring element into the retracted position out of engagement with the respective first and second positioning apertures.

2. An assembly according to claim 1
wherein the base comprises a cabinet enclosing a centrifuge.

3. An assembly according to claim 2
wherein a process controller for the centrifuge are supported on the upper weight bearing end of the support pole.

4. An assembly according to claim 1
wherein the collar includes an opening aligned with the guide passage, wherein the handle end of the pin passes through the opening, and wherein the opening and the operative end of the pin interfere to prevent passage of the operative end of the pin through the opening.

* * * * *

UNITED STATES PATENT AND TRADEMARK OFFICE
CERTIFICATE OF CORRECTION

PATENT NO. : 5,549,264
DATED : August 27, 1996
INVENTOR(S) : Richard L. West

It is certified that error appears in the above-indentified patent and that said Letters Patent is hereby corrected as shown below:

Column 2, Line 67        Delete "be" after "can"

Column 4, Line 2         Delete "facilitation" and insert --- facilitating ---

Signed and Sealed this

Twenty-fifth Day of February, 1997

Attest:

BRUCE LEHMAN

*Attesting Officer*    *Commissioner of Patents and Trademarks*